(12) United States Patent
Routray et al.

(10) Patent No.: US 12,154,679 B2
(45) Date of Patent: Nov. 26, 2024

(54) ENHANCED LIQUID CONTAINER FOR LIQUID AUTHENTICATION

(71) Applicant: Merative US L.P, Ann Arbor, MI (US)

(72) Inventors: Ramani R. Routray, San Jose, CA (US); Bruce Light Hillsberg, San Carlos, CA (US); Venkat K. Balagurusamy, Suffern, NY (US); Ashwin Dhinesh Kumar, Ossining, NY (US); Donna N Eng Dillenberger, Yorktown Heights, NY (US); Mark Dudman, Seabrook Beach, NH (US)

( * ) Notice: Subject to any disclaimer, the term of this patent is extended or adjusted under 35 U.S.C. 154(b) by 1046 days.

(21) Appl. No.: 17/099,040

(22) Filed: Nov. 16, 2020

(65) Prior Publication Data
US 2022/0157437 A1    May 19, 2022

(51) Int. Cl.
| | | |
|---|---|---|
| *B65D 41/04* | (2006.01) | |
| *A61J 1/14* | (2023.01) | |
| *G06T 3/4076* | (2024.01) | |
| *G16H 10/60* | (2018.01) | |
| *G16H 20/10* | (2018.01) | |
| *G16H 30/20* | (2018.01) | |
| *G16H 30/40* | (2018.01) | |

(52) U.S. Cl.
CPC ............ *G16H 30/40* (2018.01); *A61J 1/1418* (2015.05); *G06T 3/4076* (2013.01); *G16H 10/60* (2018.01); *G16H 20/10* (2018.01); *G16H 30/20* (2018.01)

(58) Field of Classification Search
CPC ....... A61J 1/1412; G02B 27/027; G02B 7/02; B65D 41/04; B65D 41/0407; B65D 41/0414; B65D 41/0421; B65D 41/0428; B65D 41/06; B65D 41/08; G16H 20/10; G16H 30/20

See application file for complete search history.

(56) References Cited

U.S. PATENT DOCUMENTS

| | | | | |
|---|---|---|---|---|
| 3,679,085 A | | 7/1972 | Gach | |
| 6,007,778 A | * | 12/1999 | Cholewa | ............... B01L 3/5082 422/534 |

(Continued)

FOREIGN PATENT DOCUMENTS

| | | |
|---|---|---|
| CN | 2476524 Y | 2/2002 |
| CN | 1621886 A | 6/2005 |

(Continued)

OTHER PUBLICATIONS

"Patent Cooperation Treaty PCT Notification of Transmittal of the International Search Report and the Written Opinion of the International Searching Authority, or the Declaration", International application No. PCT/IB2021/060441, International filing date Nov. 11, 2021 (Nov. 11, 2021), Priority Date Nov. 16, 2020 (Nov. 16, 2020.), 9 pages.

(Continued)

*Primary Examiner* — Ryan D Howard
(74) *Attorney, Agent, or Firm* — Stephen J. Walder, Jr.

(57) ABSTRACT

An approach for providing a cap with an embedded high-resolution lens and a sampling insert that is used during an authentication of a composition of a liquid in a container sealed by the cap. The cap has a top portion of a cap with an opening, a sampling insert inside the opening in the top portion of the cap, and a high-resolution lens inside an opening in the sampling insert.

23 Claims, 8 Drawing Sheets

(56) References Cited

U.S. PATENT DOCUMENTS

| | | | |
|---|---|---|---|
| 6,112,920 | A | 9/2000 | Lahaussois |
| 6,361,136 | B1 | 3/2002 | Watanabe |
| 6,667,936 | B1 | 12/2003 | Ditzig |
| 7,154,102 | B2 | 12/2006 | Poteet |
| 7,370,797 | B1 | 5/2008 | Sullivan |
| 8,498,052 | B2 | 7/2013 | Moon |
| 8,586,928 | B2 | 11/2013 | Sinbar |
| 8,844,722 | B2 * | 9/2014 | Wang ............... B65D 75/522 |
| | | | 220/602 |
| 8,859,969 | B2 | 10/2014 | Micheels |
| 9,031,853 | B2 | 5/2015 | Bartfeld |
| 10,322,064 | B2 | 6/2019 | Mehregany |
| 10,533,984 | B2 * | 1/2020 | Balagurusamy ....... G01N 11/00 |
| 2003/0136753 | A1 | 7/2003 | Biesecker |
| 2019/0170724 | A1 * | 6/2019 | Balagurusamy ....... G06V 10/56 |

FOREIGN PATENT DOCUMENTS

| | | |
|---|---|---|
| CN | 201961686 U | 9/2011 |
| CN | 103543205 A | 1/2014 |
| CN | 104848841 A | 8/2017 |
| CN | 211263229 U | 8/2020 |
| EP | 1601956 A2 | 12/2005 |

OTHER PUBLICATIONS

Shi et al., "A 5G-V2X Based Collaborative Motion Planning for Autonomous Industrial Vehicles at Road Intersections," 2018 IEEE International Conference on Systems, Man, and Cybernetics (SMC), Miyazaki, Japan, 2018, 5 Pages, doi: 10.1109/SMC.2018.00634.

* cited by examiner

ENHANCED LIQUID CONTAINER FOR LIQUID AUTHENTICATION

BACKGROUND

The present invention relates generally to the field of packaging liquids, and more particularly to providing enhanced packaging for authentication of a liquid medicine in a container with a high-resolution optical lens embedded in either the container cap or the bottom of the container holding the liquid medicine.

In medicine, significant time and research go into determining the best medicine to treat a medical condition or an illness. Typically, pharmaceutical companies devote large amounts of research determining which active ingredients provide the best patient outcomes for a specific medical condition and how much of the various active ingredients are needed for optimal patient outcomes. The correct dosage of the identified optimal active ingredients in a medicine for a medical condition or illness, such as cancer, provides a patient with the best opportunity for recovery.

SUMMARY

Embodiments of the present provide a lens embedded in a cap that seals a container holding a liquid. The cap includes a flat round top portion of a cap with a circular opening in the cap and the lens embedded inside the circular opening in the cap.

Embodiments of the present provide a high-resolution lens and a sampling insert embedded in a cap where the cap seals a container holding a liquid. The cap includes a top portion of the cap with an opening holding the sampling insert inside the opening in the top portion of the cap. The sampling insert embedded in the cap includes an opening that holds the high-resolution lens inside the opening in the sampling insert.

Embodiments of the present provide a liquid container with a high-resolution lens embedded in a bottom portion of the liquid container where an opening in the bottom portion of the liquid container holds the high-resolution optical lens embedded in the opening in the bottom portion of the liquid container.

A method of testing a first liquid in a first container with a high-resolution lens in a bottom portion of the first container where the method includes placing the first container with the high-resolution lens in the bottom portion of the first container in a test box with the high-resolution lens in the bottom portion of the first container positioned over an opening in a bottom portion of the test box. The method includes positioning a digital image capture device under the test box, wherein the digital imaging device is positioned under the opening in the bottom portion of the test box and under the high-resolution lens in the bottom portion of the container and capturing a first high-resolution digital image of the first liquid in the first container through the high-resolution lens in the bottom portion of the container.

Embodiments of the present invention provide a computer program for testing a liquid in a container where the computer program retrieves a high-resolution digital image of a first liquid in a first container and performs a first image analysis of the first high-resolution digital image of the liquid in the container. The computer program retrieves a result of a second image analysis of a second high-resolution digital image of a known good sample of a second liquid in a second container and compares the result of the first image analysis of the first high-resolution digital image of the first liquid in the first container to the result of the second image analysis of the second high-resolution digital image of the known good sample of the second liquid in the second container. Furthermore, the computer program determines whether the result of the first image analysis of the first high-resolution digital image of the first liquid in the first container and the result of the second image analysis of the second high-resolution digital image of the known good sample of the second liquid match.

DETAILED DESCRIPTION

Figure 1:
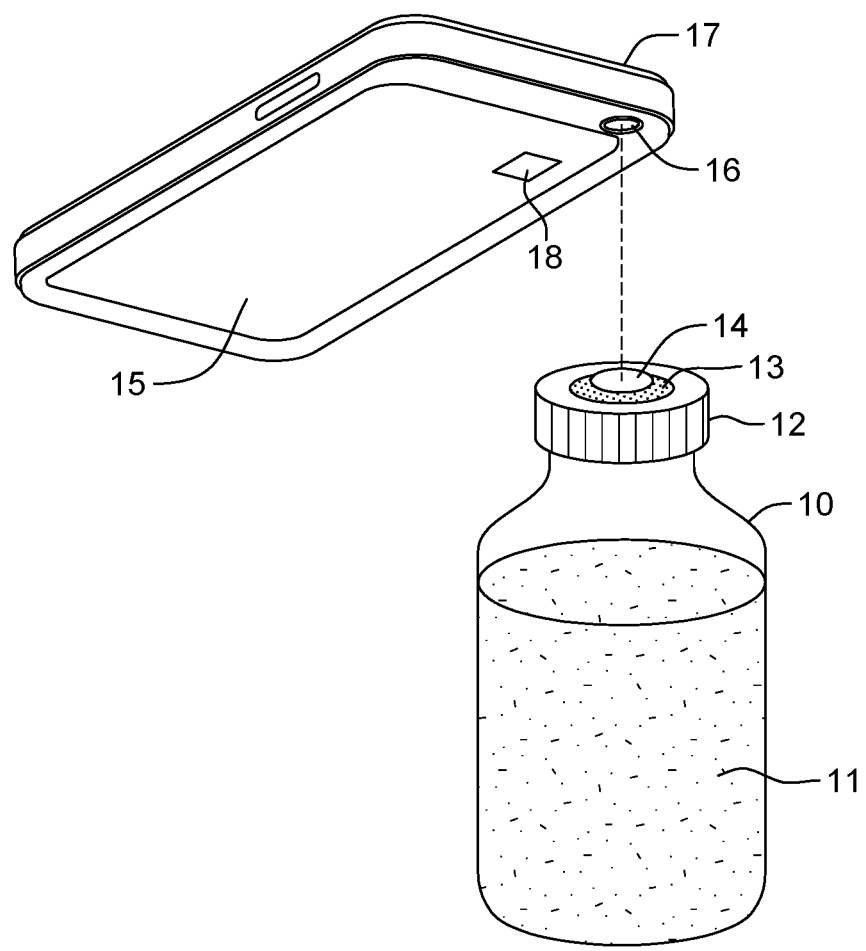
FIG. 1 is diagram illustrating a smart phone with a smart phone camera capturing an image of a liquid medicine through a cap with an embedded optical lens, in accordance with at least one embodiment of the invention.

Embodiments of the present invention recognize that counterfeit medicine is a significant problem. The exact scale of counterfeit medicine in supply chains to hospitals, clinics, and doctors is unknown but, one analysis of one hundred studies of various medicines from 2006 to 2016 evaluating more than forty-eight thousand medicine samples determined that almost ten percent of medicines sent to middle-low income countries were substandard or counterfeit. Counterfeit medicines are medicines without the required amounts of the specified active ingredient or without the correct active ingredients. Embodiments of the present invention recognize that medicine that does not provide either the correct active ingredients or the correct amount of each of the active ingredients reduces a patient's ability to recover from an injury or illness.

Embodiments of the present invention recognize that the distribution of substandard medicines or counterfeit medicines that do not provide the correct active ingredients in the correct dosages is harmful to patients. Embodiments of the present invention recognize that an apparatus and a method of quickly testing a liquid medicine without the use of a laboratory to verify that the liquid medicine has the correct active ingredients in the correct dosage is desirable for attaining optimal patient outcomes. Additionally, embodiments of the present invention recognize that providing a method of testing the liquid medicine in a vial or container without opening the container would be desirable for ensuring the medicine container seal integrity and the medicine shelf-life. Embodiments of the present invention recognize that a container that allows non-destructive testing of a liquid medicine to verify that the liquid medicine has the correct active ingredients and the correct dosage of the active ingredients without opening the container would be beneficial to the patients and especially to patients requiring critical life-saving medicine, such as cancer medicines. Embodiments of the present invention recognize an ability to authenticate that a liquid medicine has the correct active ingredients at the required dosage could be lifesaving for critical care patients diagnosed with cancer or other fast progressing diseases.

Embodiments of the present invention provide an embedded high-resolution lens in an opening in the top portion of a cap that seals a container or a vial holding a liquid, such as, a liquid medicine. The transparent high-resolution lens embedded in an opening in the top portion of the cap provides an unobstructed view of the liquid inside the vial. Embodiments of the present invention provide the embedded high-resolution lens in the cap that seals a container holding any type of liquid including a liquid medicine, a liquid chemical, or a liquid consumer product, such as, wine or perfume.

Embodiments of the present invention provide a sampling insert around the embedded high-resolution lens in the cap of the container holding the liquid medicine. The sampling insert provides an area in the cap that is adjacent to the high-resolution lens where a syringe can be inserted through the sampling insert. Once inserted into the container, the syringe removes a sample of the liquid medicine for quality testing using known chemical testing processes.

The cap with the embedded high-resolution lens sealing the container holding a liquid medicine allows a digital image of the liquid medicine in the vial to be captured through the high-resolution lens in the cap by a digital imaging device or a camera in a smart phone positioned above the high-resolution optical lens in the cap. Embodiments of the present invention provide a method for the digital image of the liquid medicine in the vial to be retrieved by an application in the smart phone or by a program in another computing device. The application in the smart phone or the program in another computing device uses known digital image analysis techniques, such as a hue, saturation, value (HSV) color space analysis or color analysis and/or a red-green-blue (RGB) color space analysis, to perform an analysis of the liquid medicine in the vial. As known to one skilled in the art, a "color space" is any mathematical representation of perceived colors where the HSV color space has three color dimensions, comprising hue (H), saturation (S), and value (V). In an HSV color space, the principal wavelength expressed by a color is entirely represented by hue, saturation defines the brilliance and intensity of a color (e.g., specifies how pure or gray a color is), and value specifies the brightness of the color. The RGB color space has three color dimensions, comprising red (R), green (G), and blue (B). In digital imaging, any digitally recorded color can be expressed by a unique combination of these three values and almost all digital imaging devices, including digital cameras and image scanners, use the RGB color space to store colors in image files as numerical values. In both a HSV color space analysis or a RGB color space analysis, each of these characteristics (e.g., hue, saturation, and value or red, green, and blue) has a finite range of possible values, and therefore the entire color space can be represented by a three dimensional graph with its three axes representing the three characteristics. Various computer programs and software have been developed to employ HSV and RGB color space analysis.

Embodiments of the present invention provide a method for the computer program to compare the results of the digital image analysis of the captured high-resolution digital image of the medicine in the vial to the results of a digital image analysis of high-resolution digital images of authentic or known good samples of the liquid medicine taken under the same conditions. The computer program provides a comparison of digital image attributes, such as HSV of the high-resolution digital images of the liquid medicine in the container and the digital image attributes of the high-resolution digital images of known good or authentic liquid samples of the liquid medicine to determine whether the liquid medicine in the container is authentic or good.

A liquid chemical compound or a liquid medicine that is authentic (e.g., not counterfeit) has the required active ingredients in the required amount for each of the active ingredients. A counterfeit liquid or liquid medicine is a liquid or a liquid medicine that does not have one or more of the required active ingredients and/or does not have the proper amount (i.e., the correct dosage) of one or more of the active ingredients of the liquid or liquid medicine. When the results of the comparison of the results of the digital image analysis of the liquid medicine in the container to be evaluated and the results of the digital image analysis of the known good sample of the liquid medicine match, then the computer program determines that the liquid medicine in the container is authentic or good. A liquid medicine that is determined to be authentic or good will provide patients with the best possible outcome in overcoming illness or injury when properly taken by the patient.

Embodiments of the present invention utilize a mobile computing device or smart phone with a high-quality camera placed precisely over the high-resolution lens embedded in the cap to capture high-resolution digital images of the liquid medicine in the container sealed by the cap. Embodiments of the present invention provide a method of analyzing the captured high-resolution digital image of the liquid medicine using one or more known digital image analysis methods in an application on the smart phone.

Additionally, embodiments of the present invention provide a high-resolution lens that is embedded in the bottom of the container or vial holding a liquid or a liquid medicine. Embodiments of the present invention capture high-resolution digital images of the liquid medicine in the container through the high-resolution lens embedded in the bottom of the container. Embodiments of the present invention capture high-resolution digital images of the liquid medicine in the container by a digital imaging device or a camera in a smart phone that is placed or held under the high-resolution optical lens in the bottom portion of the container.

Embodiments of the present invention include a computer program or an application in the smart phone that retrieves and analyzes the high-resolution digital images of the liquid medicine in the container using one or more known digital imaging analysis techniques. Embodiments of the present invention provide a method for the application in the smart phone to retrieve high-resolution digital images of one or more known good samples of the liquid medicine taken under the same conditions as the liquid medicine in the container. The application in the smart phone uses the same known digital image analysis techniques on the high-resolution digital images of the known good samples of the liquid medicine as used on the high-resolution digital images of the liquid medicine to be authenticated or evaluated.

Embodiments of the present invention provide a method for the application to compare the results of digital image analysis of the digital images of the known good samples of the liquid medicine to the results of the digital image analysis of the digital images of the liquid medicine in the container to be authenticated. The comparison of the results of the digital image analysis of the liquid medicine in the container to the results of the digital image analysis of the authentic or known good sample of the liquid medicine determines if the liquid medicine in the container that is being evaluated is authentic or if the liquid medicine in the container being evaluated is counterfeit.

Embodiments of the present invention provide a test box with an opening in the bottom portion of the test box that is capable of holding a container of a liquid medicine inside the test box. The container has a high-resolution lens embedded in an opening in the bottom of the container. Embodiments of the present invention provide the test box that positions the high-resolution lens embedded in the bottom of the container directly above the opening in the bottom of the test box. Embodiments of the present invention provides guides under the test box to precisely position a digital imaging device or a smart phone under the opening in the test box and under the high-resolution optical lens embedded in the container. The smart phone or digital imaging device capture high-resolution digital images of the liquid medicine in the container through the embedded high-resolution lens in the bottom of the container. Embodiments of the present invention provide an application in the smart phone that retrieves the digital image data of the liquid medicine in the container for digital image analysis and comparison with retrieved digital image analysis of known good samples of the liquid medicine.

The present invention will now be described in detail with reference to the Figures.

FIG. 1 is diagram illustrating camera 16 in smart phone 17 capturing an image of medicine 11 in vial 10 with cap 12, in accordance with at least one embodiment of the invention. As depicted, cap 12 includes optical lens 14 and sampling insert 13. In other embodiments, vial 10 is another type of a liquid packaging container, such as, a bottle, tube, a single-use container, or other liquid package capable of being sealed by cap 12 with optical lens 14. In some embodiments, vial 10 is transparent.

In various embodiments, medicine 11 is a liquid medicine. In some embodiments, medicine 11 is another type of liquid. For example, medicine 11 is a liquid chemical other than a medicine. In these embodiments, medicine 11 may be a liquid, such as, a single component chemical liquid, a chemical liquid composed of several chemicals (e.g., hydrolytic fluid), or a high-end liquid consumer product (e.g., wine, perfume, etc.).

In various embodiments, cap 12 is a twist-on cap with an opening containing optical lens 14. In other embodiments, cap 12 is one of a locking hinged top, a pressure release top (e.g., with side actuation), a child-proof cap, a stopper, such as, a rubber or cork stopper for a bottle or a tube. As depicted, cap 12 seals vial 10 containing medicine 11. In various embodiments, cap 12 has a flat circular top portion with an opening holding sampling insert 13 and optical lens 14. The opening in cap 12 is depicted as round but may be any geometric shape, such as rectangular. For example, the opening in cap 12 may be rectangular when sampling insert 13 has a rectangular outer edge shape. In various embodiments, optical lens 14 is inside an opening in sampling insert 13. Cap 12 includes a tubular portion attaching to the circular flat top portion of cap 12. The tubular portion of cap 12 extends downward with a set of threads on an inside surface of the tubular portion of cap 12. Using known sealing methods for twist tops, the set of threads on an outside edge of the mouth or opening in vial 10 match up with the set of threads on cap 12 to provide a liquid and air-tight seal of vial 10 when cap 12 twisted in place sealing vial 10. The circular flat top portion of cap 12 and the tubular portion of the cap 12 can be formed with a known type of medicine cap material, such as, rubber, plastic, hard silicone, or metal. In other embodiments, cap 12 does not have threads or a tubular threaded portion. For example, cap 12 can have side actuators to release a press-on cap.

In various embodiments, cap 12 with optical lens 14 is a re-usable cap. For example, a customer or patient can return cap 12 to a pharmacy where they purchased medicine 11 or mail cap 12 back to the manufacturer or supplier of medicine 11. In some cases, a return envelope is provided with purchased medicine 11. In other cases, a deposit, for example, five dollars, is included in the purchase price of medicine 11 that is credited back to the purchaser upon a return of cap 12 with optical lens 14. In these embodiments, cap 12 with optical lens 14 is capable of withstanding required cleaning and sanitation processes for the re-use of cap 12.

In various embodiments, sampling insert 13 is inside an opening in the top of cap 12 and surrounds optical lens 14. In various embodiments, sampling insert 13 is composed of a soft material that allows insertion of a syringe or similar sharp instrument through sampling insert 13 in cap 12 in an area adjacent to optical lens 14. The insertion of a syringe through sampling insert 13 allows the syringe to remove a sample of medicine 11. Using known sampling methods, the syringe can pull a sample of a liquid or medicine in the container sealed by cap 12 without opening the liquid container or vial. When sampling insert 13 is used to withdraw a sample of medicine 11 as another or alternative method of testing medicine 11, the sample of medicine 11 may be tested, for example, using known chemical analysis methods to determine the active ingredients, the amount of the active ingredients, and/or to determine if contaminates are present in medicine 11. Sampling insert 13 can be composed of any plastic, rubber, silicone material, or another material commonly used to provide an area for syringe insertion into vial 10. While depicted as circular in shape with a circular opening for optical lens 14, in other embodiments, sampling insert 13 has a rectangular outer edge shape with an interior circular opening that holds optical lens 14 in cap 12. Embedding optical lens 14 into sampling insert 13 in cap 12 provides a new method of providing an optical test of medicine 11 in addition to traditional ingredient testing of medicine 11 sample removed using sampling insert 13.

In various embodiments, medicine 11 is liquid medicine in vial 10 or another packaging container (e.g., a bottle, tube, or other liquid package). Medicine 11 can be a high-value and/or patient critical drug such as a chemotherapy drug (e.g., docetaxel, cytarabine, methotrexate, etc.). In some embodiments, medicine 11 is a non-medicinal liquid in a container, such as, vial 10. For example, medicine 11 can be a wine, a perfume, a high value liquid product, a liquid chemical or a liquid compound chemical product that could be counterfeit (e.g., packaged without the appropriate ingredients or correct composition).

In various embodiments, optical lens 14 is a high-resolution lens capable of being embedded or held in an opening formed in the top portion of cap 12. Optical lens 14 provides a non-intrusive ability (e.g., without opening vial 10) to observe and capture detailed digital images of medicine 11 in vial 10. By placing camera 16 over optical lens 14 in cap 12, one or more high-resolution digital images of medicine 11 in vial 10 may be captured. In various embodiments, optical lens 14 is a high-resolution lens with a micron or a sub-micron resolution. Optical lens 14 can be any high-resolution lens capable of being embedded or included in cap 12. In other embodiments, an optical lens similar to optical lens 14 is embedded in a portion of vial 10 such as a side or a bottom of vial 10 or in another container directly holding medicine 11 (depicted in FIG. 3A).

In one embodiment, optical lens 14 is magnifying lens (0.5× to 3× magnification) with a high-resolution (1 micron or smaller). In one embodiment, more than one optical lens 14 is embedded in cap 12. For example, optical lens 14 is a set of two optical lens 14. In this embodiment, optical lens 14 includes two optical lens 14 embedded with one lens over the other lens in the opening in cap 12. In this example, the resolution of one or more both lens of optical lens 14 may not be a micron or less (e.g., lower resolution). While in some embodiments, optical lens 14 is a biconcave lens, optical lens 14 can be a lens with of any type of curved surface, such as, plano-concave lens or other specialized lens such as an aspheric or hybrid aspheric lens capable of magnifying a view of medicine 11 and providing a high-resolution image of medicine 11.

As depicted, optical lens 14 is circular with a disk-like shape. In various embodiments, the outer edges of optical lens 14 provide a small flat surface around the outside edge of optical lens 14 but, optical lens 14 is not limited to this shape (e.g., may be a disk without flattened edges, etc.). Optical lens 14 can be composed of any material used in a high-resolution lens, such as, glass, plastic, or quartz. As depicted, the diameter of optical lens 14 is greater than the opening in sampling insert 13 (e.g., optical lens 14 is embedded in sampling insert 13). In various embodiments, optical lens 14 is embedded or held in the center of cap 12 however, optical lens 14 is not limited to this location (e.g., optical lens 14 may not be centered in cap 12 in other embodiments).

As depicted in FIG. 1, smart phone 17 includes image analysis application 18, camera 16, and user interface (UI) 15. In other embodiments, smart phone 17 is any type of mobile computing device or digital imaging device that includes an ability to capture high-resolution digital images of medicine 11. For example, smart phone 17 can be a tablet, a smart watch, augmented reality (AR) glasses, a smart camera, or a notebook computer including digital imaging capability. While depicted with camera 16 on the same side of smart phone 17 as UI 15, in some embodiments, camera 16 resides on the backside of smart phone 17 (e.g., opposite UI 15 as depicted in FIG. 5B). Using known smart phone technology, in various embodiments, camera 16 captures digital images from either side of smart phone 17. Using known user interface technology, UI 15 provides an interface for communication between a user of smart phone 17 with camera 16, smart phone 17, image analysis application 18, and other computing devices (not depicted). In various embodiments, UI 15 displays a view of medicine 11 in vial 10.

In some embodiments, smart phone 17 with camera 16 captures high-resolution digital images of medicine 11 using optical lens 14 in cap 12 that are retrieved by a digital image analysis program operating on another computer device (e.g., a test system, a desktop computer, mainframe computer, or a computing device in a cloud computing environment not depicted in FIG. 1) for digital image analysis of the high-resolution digital images of medicine 11. The computer program on another computing device executes similar to digital analysis application 18 and can verify that the correct active ingredients are present in medicine 11 with the correct amount of each of the active ingredients using digital image analysis of the high-resolution digital images of medicine 11 in vial 10 and high-resolution digital images of known good samples of medicine 11.

In one embodiment, the functionality of smart phone 17 is included in a test system. The test system can include a computing device capable of executing a computer program to analyze the high-resolution digital images of medicine 11 and a digital imaging device. In this example, the computer program in the test system that provides the functionality of image analysis application 18 and the digital imaging device provides the ability of camera 16 to capture high-resolution digital images of medicine 11. The test system may include additional features such as positioning hardware to hold optical lens 14 directly under the digital imaging device. In other words, the test system has the ability to capture the high-resolution digital images of medicine 11 and includes computer algorithms and code capable of executing the functionality similar to digital image application 18 to verify if medicine 11 in vial 10 is authentic or counterfeit.

Camera 16 can be any type of digital imaging device capable of capturing high-resolution digital images of medicine 11. In various embodiments, camera 16 is a smart phone camera capable of capturing high-resolution digital images of medicine 11. The high-resolution digital images of medicine 11 captured by camera 16 include digital image characteristics such as hue, saturation, and value which can be used in the determination of a counterfeit sample of medicine 11 in vial 10. In various embodiments, camera 16 is capable of capturing digital images with a resolution of a micron or less. In one embodiment, camera 16 is in a test system. In some embodiments, camera 16 is integrated into another mobile computing device, such as a tablet. In an embodiment, camera 16 is a standalone digital camera capable of capturing high-resolution digital images for distribution to or retrieval by another computing device. For example, high-resolution images of medicine 11 captured by camera 16 can be transmitted to other computing devices, by downloading, wireless transmission, or by a storage medium, such as, a memory stick or similar memory storage device, to a image analysis application 18 or program in another computer (not depicted in FIG. 1).

In various embodiments, camera 16 captures high-resolution digital images of medicine 11 in vial 10 to be evaluated for authentication and captures high-resolution digital images of known good samples of medicine 10 in another vial 10 using the same set of conditions and settings (e.g., the same lighting, distance to medicine 11, shutter speed, etc.). Using the same set of conditions and the same settings in camera 16 to capture high-resolution digital images of both medicine 11 in vial 10 to be authenticated and known good samples of medicine 11 in another vial 10 provides a good comparison of the results of digital image analysis of a known good sample of medicine 11 to medicine 11 in vial 10 being tested to determine if medicine 11 in vial 10 being evaluated is authentic.

Figure 5A:
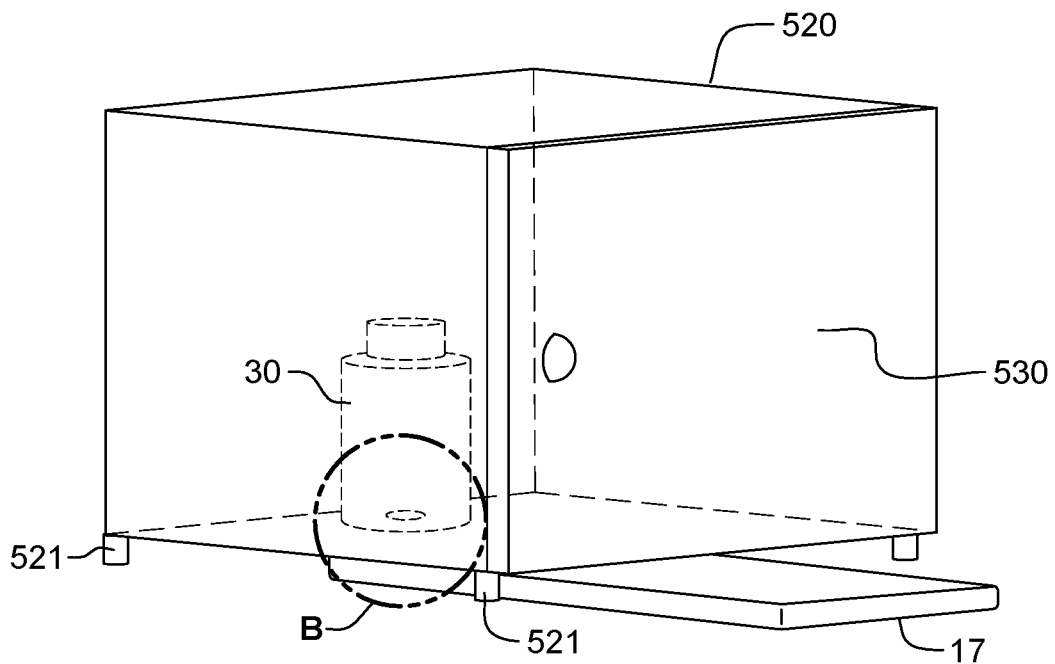
FIG. 5A is an illustration of a test box with a breakout showing a liquid chemical in the vial with the embedded optical lens, in accordance with at least one embodiment of the invention.
Figure 5A:
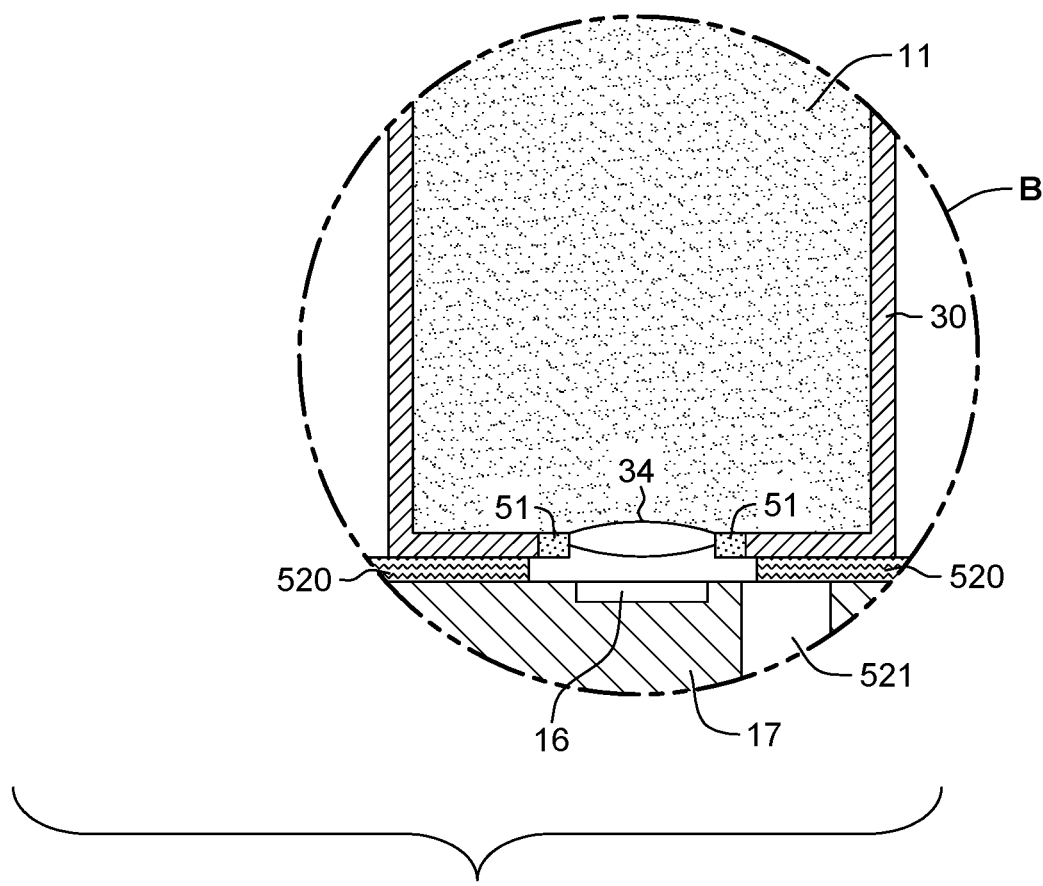
Figure 5B:
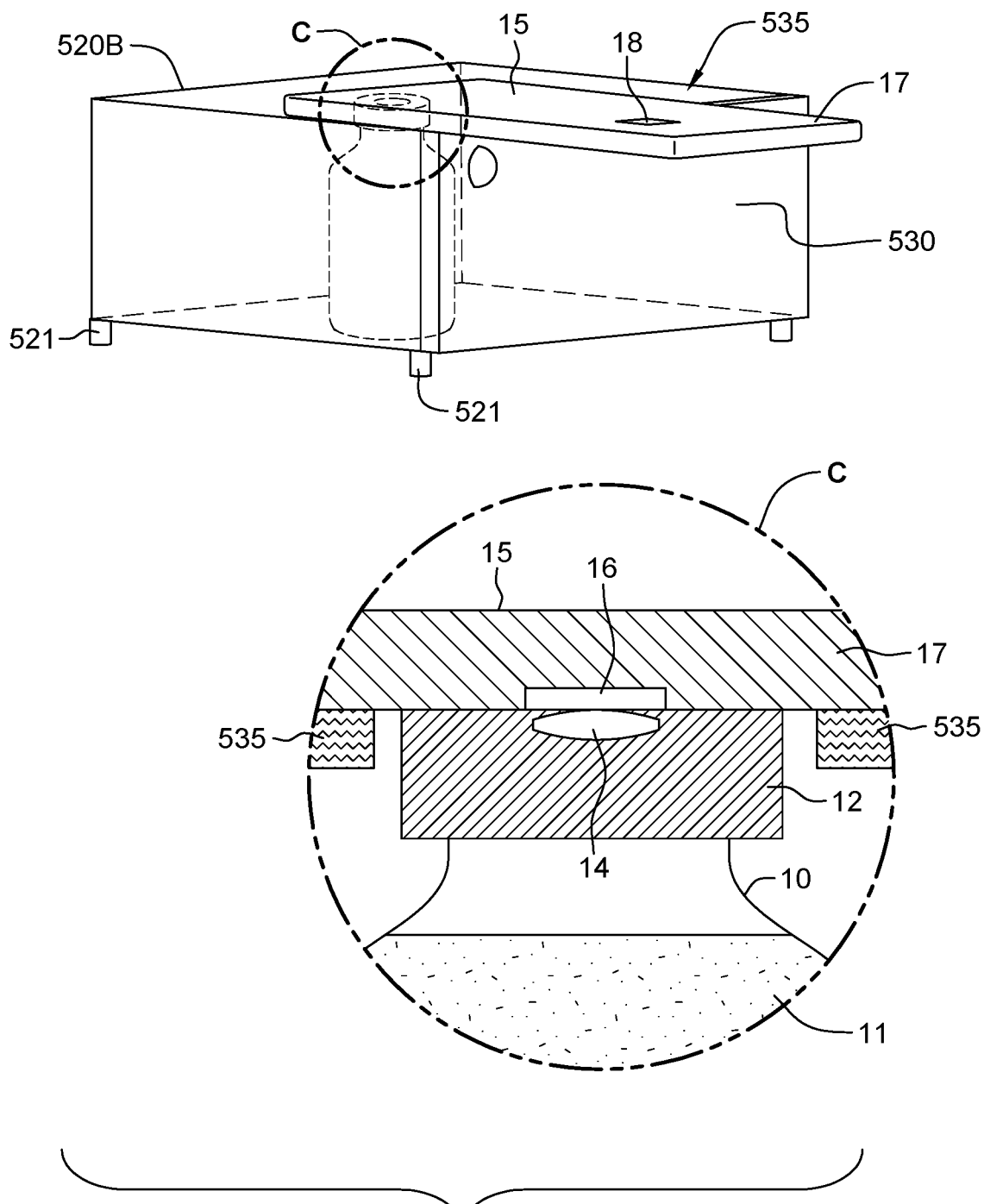
FIG. 5B is an illustration of a test box with a breakout showing the liquid medicine in the vial sealed with the cap with the embedded optical lens, in accordance with at least one embodiment of the invention.

While depicted as a smart phone 17 with camera 16 being held over optical lens 14 of cap 12, in other embodiments, camera 16 is fixed directly over optical lens 14 by a test fixture or test box (depicted in FIG. 5B), placed in a test box under optical lens 14 when vial 10 is upside down in the test box or test fixture, or placed under a vial with an embedded optical lens in the bottom of the vial (depicted in FIG. 5A).

In various embodiments, digital analysis application 18 receives a user input on UI 15 to retrieve high-resolution images of medicine 11 in vial 10 captured by camera 16. Image analysis application 18 includes known digital image analysis algorithms and computer code capable of providing detailed digital image analysis of high-resolution digital images of medicine 11. In some embodiments, image analysis application 18 includes machine learning algorithms. Image analysis application 18 provides a capability to analyze high-resolution digital images and compare the results of the digital image analysis of known good samples of medicine 11 in a different vial 10 and samples of medicine 11 in vial 10 (e.g., medicine 11 to be authenticated as good) to determine whether medicine 11 in vial 10 to be authenticated is counterfeit or authentic (e.g., an authentic medicine matches the composition of the known good samples of medicine 11).

In various embodiments, image analysis application 18 uses an HSV color space to analyze the high-resolution digital images of medicine 11. As known to one skilled in the art, in a HSV color space, the principal wavelength expressed by a color is entirely represented by hue (H), saturation (S) specifies how pure or gray a color is, and value (V) specifies the brightness of the color. In some cases, when image analysis application 18 uses an HSV color space analysis of the high-resolution digital image of medicine 11, numerical values can be determined for the saturation, the hue, and the value of each pixel of the high-resolution digital image of medicine 11. In other examples, image analysis application 18 can use red, green, blue (RBG) color analysis or another known digital image analysis method. In some cases, a combination of an HSV and an RBG or other digital image analysis may be used by image analysis application 18 to analyze high-resolution digital images of medicine 11. In various embodiments, image analysis application 18 uses the same application settings to analyze digital images of medicine 11 in vial 10 being authenticated as the application setting used to analyze known good samples of medicine 11 in another vial 10. In an embodiment, digital analysis application 18 receives a user input to retrieve from persistent storage 705 (depicted in FIG. 7) in smart phone 17 or in another computing device (not depicted) a previously performed digital image analysis of high-resolution digital images of known good samples of medicine 11.

Figure 2A:
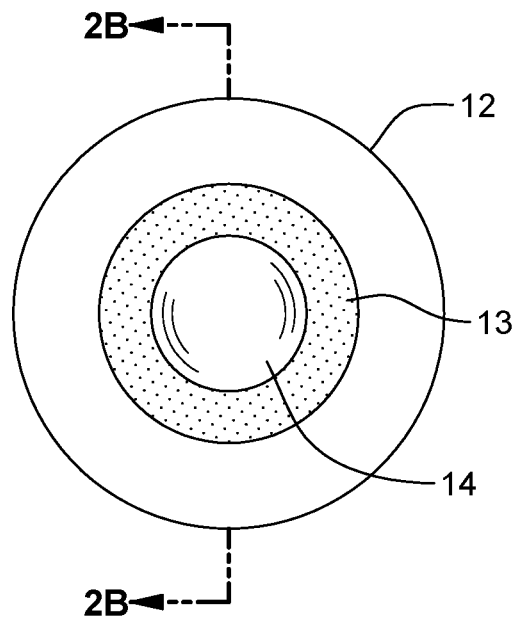
FIG. 2A is an illustration of a top view of the cap with the embedded optical lens, in accordance with at least one embodiment of the invention.

FIG. 2A is an illustration of a top view of cap 12 with optical lens 14 and sampling insert 13, in accordance with at least one embodiment of the invention. Cap 12 with optical lens 14 can be used during an authentication of a composition of a liquid, such as, medicine 11 or a chemical in a container sealed by cap 12. As previously discussed, the authentication of the liquid, such as medicine 11 in FIG. 1, can occur using image analysis application 18 and a high-resolution digital image of the liquid captured through optical lens 14. As depicted, FIG. 2A includes cap 12 with an opening that holds sampling insert 13 and optical lens 14. Cap 12 may be composed any material suitable for a medicine vial cap, a medicine bottle cap, a tube cap, a stopper, a wine bottle cap or cork, a perfume bottle cap, or a cap for any other packaging container of a liquid. For example, cap 12 may be composed of a hard-plastic material such as a high-density polyethylene (HDPE), a hard rubber material, a silicone material, or a metal material.

As depicted, cap 12 includes a flat, circular top portion of cap 12. The flat, circular top portion of cap 12 has an opening holding sampling insert 13 which in turn has an opening holding optical lens 14. Cap 12 is not limited to this shape or type of cap. In other embodiments, cap 12 is a stopper, a cork, a locking cap, child proof cap or another type of cap with another shape (e.g., square, oval, or an irregular shape).

As depicted, the opening in cap 12 is circular however, in some embodiments, the opening in cap 12 is rectangular. In this case, the outer edge shape of sampling insert 13 is rectangular. When the opening in cap 12 is a rectangle or a square, the outer edges of sampling insert 13 may form a rectangular shape and inside edges of sampling insert 13 form a circular shape to hold optical lens 14.

Figure 2B:
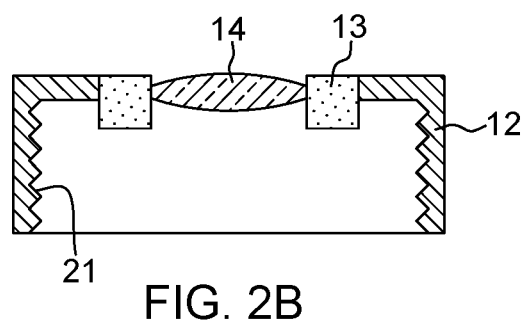
FIG. 2B is an illustration of a top view of the cap with the embedded optical lens and a sampling insert, in accordance with at least one embodiment of the invention.

FIG. 2B is a diagram of section 2B-2B of cap 12 with optical lens 14 and sampling insert 13, in accordance with at least one embodiment of the invention. Section 2B-2B is identified on FIG. 2A. As depicted as a cross-section of cap 12, FIG. 2B includes cap 12, which is a twist cap with a set of threads 21 on the inside side surfaces of cap 12. While depicted as a twist cap in FIG. 2B, cap 12 is not limited to using twist top sealing or to a twist cap in other embodiments. Threads 21 use known methods of providing a twist top seal with a similar set of threads (not depicted) that are present on the outside mouth or outside edges of an opening in a medicine vial or other liquid container. While FIG. 2B depicts an embodiment of cap 12 with optical lens 14, in other embodiments, the specific and relative thicknesses and dimensions of cap 12, optical lens 14, and threads 21 may be different than depicted in FIG. 2B.

As depicted, a thickness of sampling insert 13 is more than the thickness of optical lens 14. However, the thickness of sampling insert is not limited to the thickness depicted (e.g., may be the same as the thickness of optical lens 14, etc.). In various embodiments, the thickness and material selection of sampling insert 13 allows a syringe to be inserted through sampling insert 13. In various embodiments, sampling insert 13 acts as a gasket between the opening in cap 12 and optical lens 14 sealing optical lens 14 in cap 12 (e.g., provides an air-tight and liquid tight seal between cap 12 and optical lens 14).

Figure 2C:
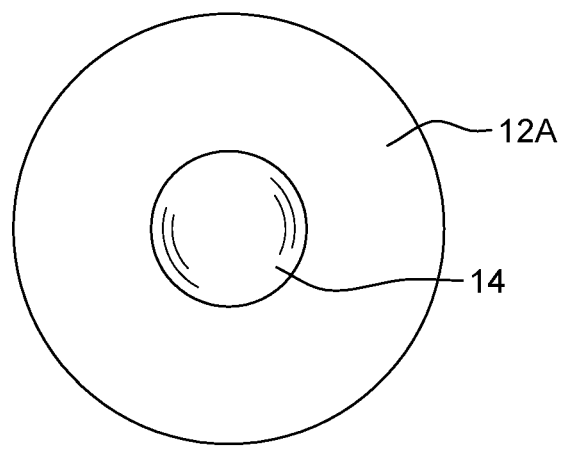
FIG. 2C is a diagram of section B-B of the cap with the embedded optical lens and the sampling insert, in accordance with at least one embodiment of the invention.

FIG. 2C is an illustration of a top view of cap 12A with optical lens 14, in accordance with at least one embodiment of the invention. As depicted, FIG. 2C includes cap 12A and optical lens 14. Cap 12A is similar to cap 12 in FIG. 1 but, cap 12A does not include sampling insert 13 depicted in FIG. 1. In various embodiments, cap 12A is a plastic cap, rubber, or metal cap with an opening to cradle or hold optical lens 14. For example, cap 12A can be HDPE or any other suitable plastic for a medicine vial cap or a medicine bottle cap. In one embodiment, cap 12A is a plastic or cork stopper for a medicine tube with embedded optical lens 14. Optical lens 14 may be embedded in cap 12A during cap 12A manufacturing or molding process. In various embodiments, cap 12A extends to surround and encompass the edges of optical lens 14 to hold optical lens 14 in place. Optical lens 14 in the opening of cap 12A allows a clear view of any liquids or medicine in a vial or container sealed by cap 12A. In an embodiment, optical lens 14 includes a soft ring or gasket (not depicted in FIG. 2C). A rubber, silicone, or other gasket like material may be present along the outside edges of optical lens 14 to prevent or reduce damage to optical lens 14 during cap 12A manufacture or if a container or vial with cap 12A is dropped.

Figure 3A:
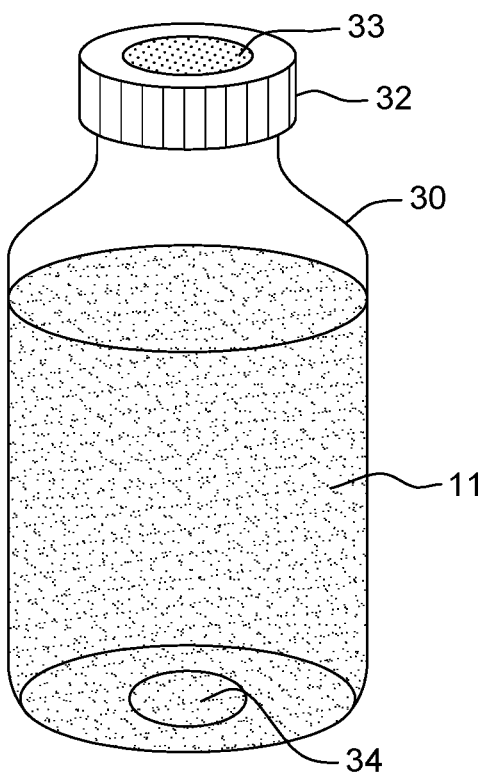
FIG. 3A is an illustration of a vial with an optical lens alternatively embedded in the bottom of the vial, in accordance with at least one embodiment of the invention.

FIG. 3A is an illustration of vial 30 holding medicine 11 with optical lens 34 embedded in the bottom of vial 30, in accordance with at least one embodiment of the invention. As depicted, FIG. 3A includes cap 32 with sampling insert 33, vial 30, medicine 11, and optical lens 34 embedded in the bottom of vial 30. Cap 32 with sampling insert 33 can be type of known cap or conventional closure mechanism for a liquid container such as a stopper, a child-proof cap, a plastic or metal cap, etc.

In various embodiments, vial 30 is a liquid container with optical lens 34 embedded in an opening in the bottom of vial 30. In various embodiments, the opening in the bottom of vial 30 is round when optical lens 34 had a round outer edge shape. In one embodiment, optical lens 34 is embedded in a side of vial 30. Vial 30 can be any type of liquid holding container that can hold medicine 11, such as, a bottle, a tube, a vial, a single use dispensing package or other liquid holding packaging container capable of having optical lens 34 embedded in a bottom portion of vial 30. In various embodiments, vial 30 is composed of a transparent material, such as, a transparent plastic, acrylic, or glass. While depicted a round container, in other embodiments, a bottom portion of vial 30 has one of a rectangular shape, a square shape, an oblong shape, a hexagonal shape, or an irregular shape (e.g., a combination of shapes). In various embodiments, optical lens 34 provides a way to capture high-resolution digital images of medicine 11 through optical lens 34 in the bottom of vial 30. The analysis of the high-resolution digital images can be done by image analysis application 18 or a computer program in another computing device using a similar method of analysis as discussed above relative to the high-resolution digital images captured through optical lens 14 embedded in cap 12 of FIG. 1.

Optical lens 34 is essentially the same as optical lens 14 discussed in detail with respect to FIG. 1. Optical lens 34 may be larger than optical lens 14, smaller than optical lens 14, or the same size. While optical lens 34 is depicted in the center of the bottom portion of vial 30, in some cases, optical lens 34 is located to the right or left of the center of vial 10 (e.g., is off-center). In some embodiments, a gasket or ring of another material (e.g., plastic, rubber, silicone, etc.) is present around the opening in vial 30 and holds optical lens 34 in place. Optical lens 34 may be a transparent, micron or sub-micron resolution lens embedded in an opening in the bottom portion of vial 30. In various embodiments, optical lens 34 provides an ability to capture a high-resolution digital image of medicine 11. A smart phone with a camera (e.g., smart phone 17 with camera 16 depicted in FIG. 1) can capture a high-resolution digital image of medicine 11 in vial 30 which may be retrieved and used by image analysis application 18 (depicted in FIG. 1) to determine if medicine 11 is authentic or counterfeit. In one embodiment, vial 30 with optical lens 34 is placed directly on smart phone 17 with optical lens 34 directly over camera 16.

In some embodiments, vial 30 with medicine 11 and optical lens 34 is placed in a test fixture or a test box for testing. An example of vial 30 in a test box with smart phone 17 is depicted in FIG. 5A. In this example, optical lens 34 in vial 30 can be precisely placed and centered over camera 16 in test box 520.

Figure 3B:
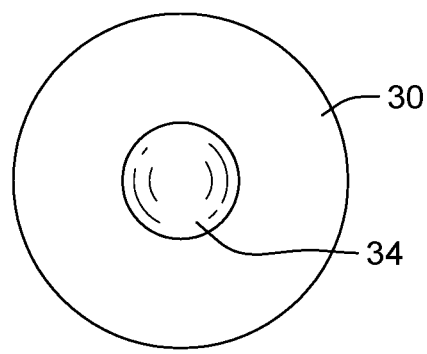
FIG. 3B is an illustration of a bottom view of the vial with the optical lens embedded in the bottom of the vial, in accordance with at least one embodiment of the invention.

FIG. 3B is an illustration of a bottom view of vial 30 with optical lens 34, in accordance with at least one embodiment of the invention. In various embodiments, optical lens 34 is centered in the bottom of vial 30. In other embodiments, optical lens 34 is not centered in the bottom of vial 30. Optical lens 34 can be a same size as optical lens 14 or a different size than optical lens 14 (e.g., optical lens 34 is smaller or larger than optical lens 14). In various embodiments, optical lens 34 is larger than the opening in the bottom of vial 30 (e.g., optical lens 34 is embedded in the bottom of vial 30). In an embodiment, a gasket is inside the opening in the bottom of vial 30 and optical lens 34 is embedded in the gasket (not depicted in FIG. 3B).

Figure 4A:
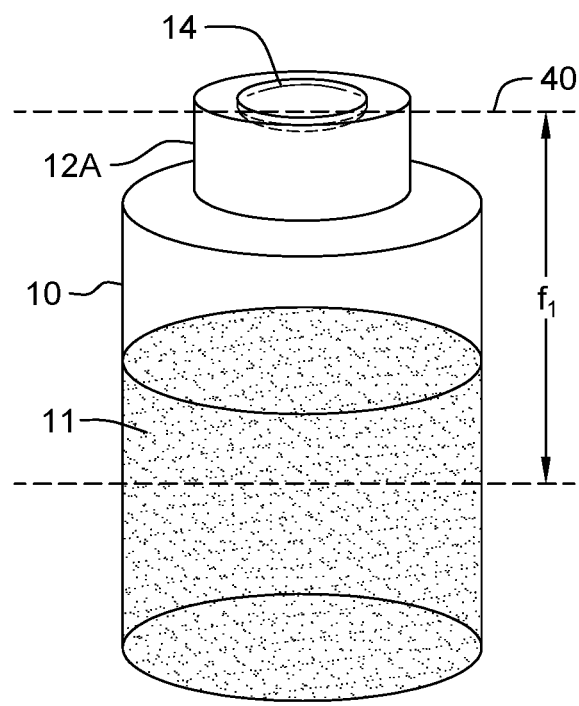
FIG. 4A is an illustration depicting a focal length of the embedded optical lens in the cap of the vial holding the liquid medicine, in accordance with at least one embodiment of the invention.

FIG. 4A is an illustration depicting a focal length $f_1$ of optical lens 14 in cap 12A of vial 10 holding medicine 11, in accordance with one embodiment of the invention. As depicted, FIG. 4A includes cap 12A with embedded optical lens 14, vial 10, and medicine 11. As previously discussed, medicine 11 can be a liquid medicine, liquid chemicals, or a liquid consumer product. FIG. 4A depicts optical lens 14 in cap 12A with lens principal plane 40 and focal length $f_1$ of optical lens 14. Cap 12A, vial 10, medicine 11, and optical lens 14 are the same as cap 12A, vial 10, medicine 11, optical lens 14 discussed previously in detail with reference to FIG. 2C. As depicted, optical lens 14 is selected with a focal length, such as $f_1$, so that focal length $f_1$ is long enough to extend into medicine 11. For example, for medicine 11 in vial 10, cap 12A has optical lens 14 with a focal length, $f_1$ of one to five centimeters. The focal length $f_1$, as known to one skilled in the art, can be determined using known focal length equations based, at least in part, on optical lens 14 selection and distance to medicine 11. In an embodiment, focal length $f_1$ is not in medicine 11. A selection of optical lens 14 can be dependent on the size of vial 10 and the distance to medicine 11 to determine focal length $f_1$. In an embodiment, focal length $f_1$ of optical lens 14 is determined, based at least in part, on the imaging capabilities of camera 16 or another digital camera capturing digital images of medicine 11.

Figure 4B:
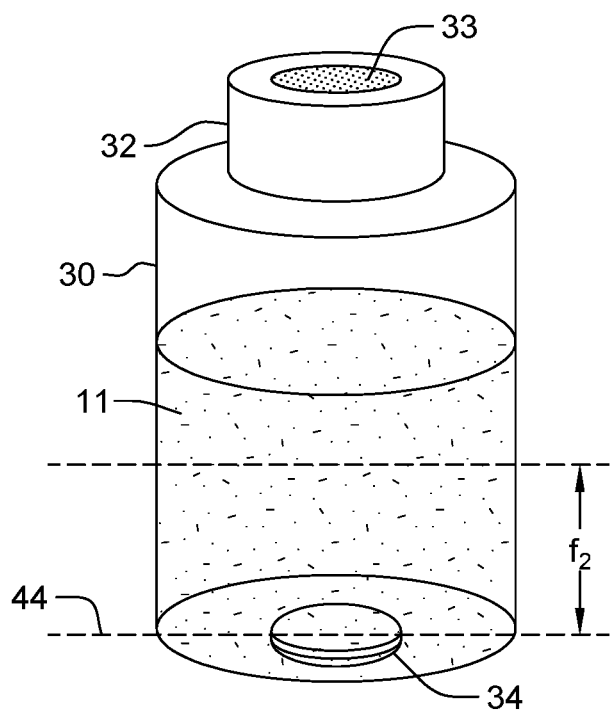
FIG. 4B is an illustration depicting a focal length of the embedded optical lens in the bottom of the vial holding the liquid medicine, in accordance with at least one embodiment of the invention.

FIG. 4B is an illustration depicting focal length $f_2$ of optical lens 34 in the bottom of vial 30 holding medicine 11, in accordance with at least one embodiment of the invention. As depicted, cap 32, sampling insert 33, vial 30, medicine 11, and optical lens 34 are the same or similar to cap 32, sampling insert 33, vial 30, medicine 11, and optical lens 34 discussed in reference to FIG. 3A. In some embodiments, a gasket or ring (depicted as gasket 51 in breakout B of FIG. 5B) surrounds optical lens 34 and is inside the opening in the bottom of vial 30. In FIG. 4B, optical lens 34 with a principal lens plane 44 provides a focal length $f_2$ from lens principal plane 44 to the focal point of optical lens 34 within the cavity space occupied by medicine 11 of vial 30. In some embodiments, focal length $f_2$ of optical lens 34 is sufficient to ensure that focal length $f_2$ of optical lens 34 is below the top surface of medicine 11. Focal length $f_2$ may be greater or less in other examples.

FIG. 5A is an illustration of test box 520 with breakout B of a portion of test box 520 with vial 30, in accordance with at least one embodiment of the invention. As depicted in FIG. 5A, breakout B depicts vial 30 with optical lens 34 surrounded by gasket 51, and medicine 11 in test box 520 and a portion of smart phone 17 and camera 16 under a bottom portion of test box 520. Test box 520 includes door 530, legs 521, and an opening or a cutout (depicted in breakout B) in the bottom of test box 520 under optical lens 34

In various embodiments, test box 520 is rectangular in shape with four vertical sides where one of the vertical sides is door 530. Additionally, as depicted, test box 520 has a top, standoffs underneath the box allowing smart phone 17 under test box 520, and a bottom with an opening that is smaller than a diameter of vial 30 but larger than optical lens 34 (e.g., the opening is greater than a diameter of optical lens 34). In some embodiments, test box 520 is composed of a transparent material, such as, an acrylic material. In this way, the sides, the top, and the bottom of test box 520 are transparent to allow light into test box 520 for capturing digital images of medicine 11. The size of test box 520 is greater than a size of vial 30. In various embodiments, the size of test box 520 is large enough to vial 30 when there is more than one size vial 30 (e.g., can hold one larger vial 30 or a smaller vial 30). In one embodiment, test box 520 includes more than one opening in the bottom of test box 520. In this case, more than one vial 30 can be placed in test box 520 and smart phone 17 can be moved such that camera 16 can capture digital images of medicine 11 in each of vial 30 in test box 520.

In various embodiments, vial 30 is placed in test box 520 with optical lens 34 above an opening in the bottom of test box 520. The opening in the bottom of test box 520 is at least as large as optical lens 34 (e.g., is larger than a diameter of optical lens 34). In various embodiments, smart phone 17 receives a user input to capture a digital image of medicine 11 through optical lens 34 which is a high-resolution optical lens. In various embodiments, test box 520 includes internal lighting or a light source inside of test box 520. In this case, the internal light source illuminates medicine 11 in order to capture the high-resolution digital image of medicine 11 with camera 16. In another example (not depicted), test box 520 is a test system or a standalone test device that includes a digital image capture device integrated with computer and/or computer processors to capture and analyze a high-resolution digital image of medicine 11.

As previously discussed, the high-resolution digital image of medicine 11 can be analyzed using a program or image analysis application 18 applying known digital image analysis methods, such as, color image analysis techniques or other known digital image analysis technique. For example, digital image analysis or an optical image analysis of the captured high-resolutions digital image uses digital image characteristics such as saturation, hue, value to provide a digital image analysis of the high-resolution digital images of medicine 11 using image analysis application 18.

In some embodiments, test box 520 includes guides (not depicted in test box 520) to hold smart phone 17 with camera 16 in position under optical lens 34 in the opening. Test box 520 also includes one or more of tabs, guides, or walls (not depicted) to precisely position vial 30 over the opening in the bottom portion of test box 520. FIG. 5A includes breakout B of test box 520 depicting vial 30 within test box 520 with camera 16 positioned under an opening in the bottom of test box 520. In this case, camera 16 is positioned directly below optical lens 34. In various embodiments, camera 16 captures high-resolution digital images of medicine 11 through optical lens 34 and the opening in the bottom of test box 520.

In another embodiment, (not depicted in FIG. 5A) vial 10 sealed by cap 12 with optical lens 14 and holding medicine 11 (depicted in FIG. 1) is placed upside down in test box 520 over camera 16. In this case, when optical lens 14 embedded in cap 12 is over the opening in the bottom of test box 520, camera 16 can capture high-resolution digital images medicine 11 through optical lens 14. When test box 520 contains an upside down vial 10 then, test box 520 may have different positioning of guides and supports (not depicted) inside test box 520 to ensure that optical lens 14 is over the opening in the bottom of test box 520 and so that upside down vial 10 does not tip over. In this case, high-resolution digital images of medicine 11 can be captured by camera 16 through optical lens 14 embedded in cap 12. Digital image analysis image application 18 may compare the captured high-resolution digital images of medicine 11 in vial 10 with high-resolution digital images of known good samples of medicine 11 to verify that medicine 11 in vial 10 has the proper ingredients and/or the correct dosage.

FIG. 5B is an illustration of test box 520B with breakout C of a portion of test box 520B that depicts vial 10 with optical lens 14 and medicine 11 inside of test box 520B, in accordance with at least one embodiment of the invention. As depicted, FIG. 5B includes; test box 520B with door 530 and top portion 535, legs 521, and an opening or cutout (depicted in breakout C) above optical lens 14. The guides used to hold smart phone 17 with camera 16 in position above optical lens 14 in the opening in test box 520B and the guides to hold vial 10 in position are not depicted. FIG. 5B includes breakout C of a portion of test box 520B that includes vial 10 with cap 12 within test box 520B and smart phone 17. As depicted, camera 16 in smart phone 17 is above the opening in a top portion 535 of test box 520B and UI 15 of smart phone 17 displays the view of camera 16 to the user. In various embodiments, camera 16 is positioned directly above optical lens 14.

In some embodiments, test box 520B does not include smart phone 17 with camera 16 but instead test box 520B and includes a high-resolution digital imaging device integrated into test box 520B. The digital imaging device, in this case, is either directly connected by wires or wirelessly connected to a computing device with a computer program capable of receiving and analyzing the high-resolution digital images of medicine 11 taken through optical lens 14. As previously discussed, the computer program includes computer code and computer algorithms with the same or greater capability as that of image analysis application 18 to provide a digital image analysis of high-resolution digital images of medicine 11 using known methods, such as, a HSV color space analysis of the high-resolution digital images of medicine 11 or a combination of digital image analyses (e.g., HSV, RGB, etc.) of the high-resolution digital images of medicine 11. In this case, the computer program integrated in test box 520B receives a user input to retrieve the digital image data of the high-resolution digital images of the known good sample of medicine 11 from the digital imaging device or storage and analyzes digital image data of the high-resolution digital images of the known good samples of medicine 11 that are taken under the same conditions as the sample of medicine 11 to be evaluated. As previously discussed, in various embodiments, the computer program can compare the results of the digital image analysis of the high-resolution digital images of medicine 11 in vial 10 to the results of the digital image analysis of the high-resolution digital images of the known good samples of medicine 11 in another vial 10 to determine if medicine 11 in vial 10 is diluted (e.g., does not provide the correct dosage).

In another embodiment, test box 520B is a test system that includes a digital camera and the computing device with the computer program capable of retrieving and analyzing the high-resolution digital images of medicine 11 taken through optical lens 14. In this embodiment, the computing program is capable of performing the same digital image analysis and comparisons as previously discussed with respect to image analysis application 18.

Figure 6:
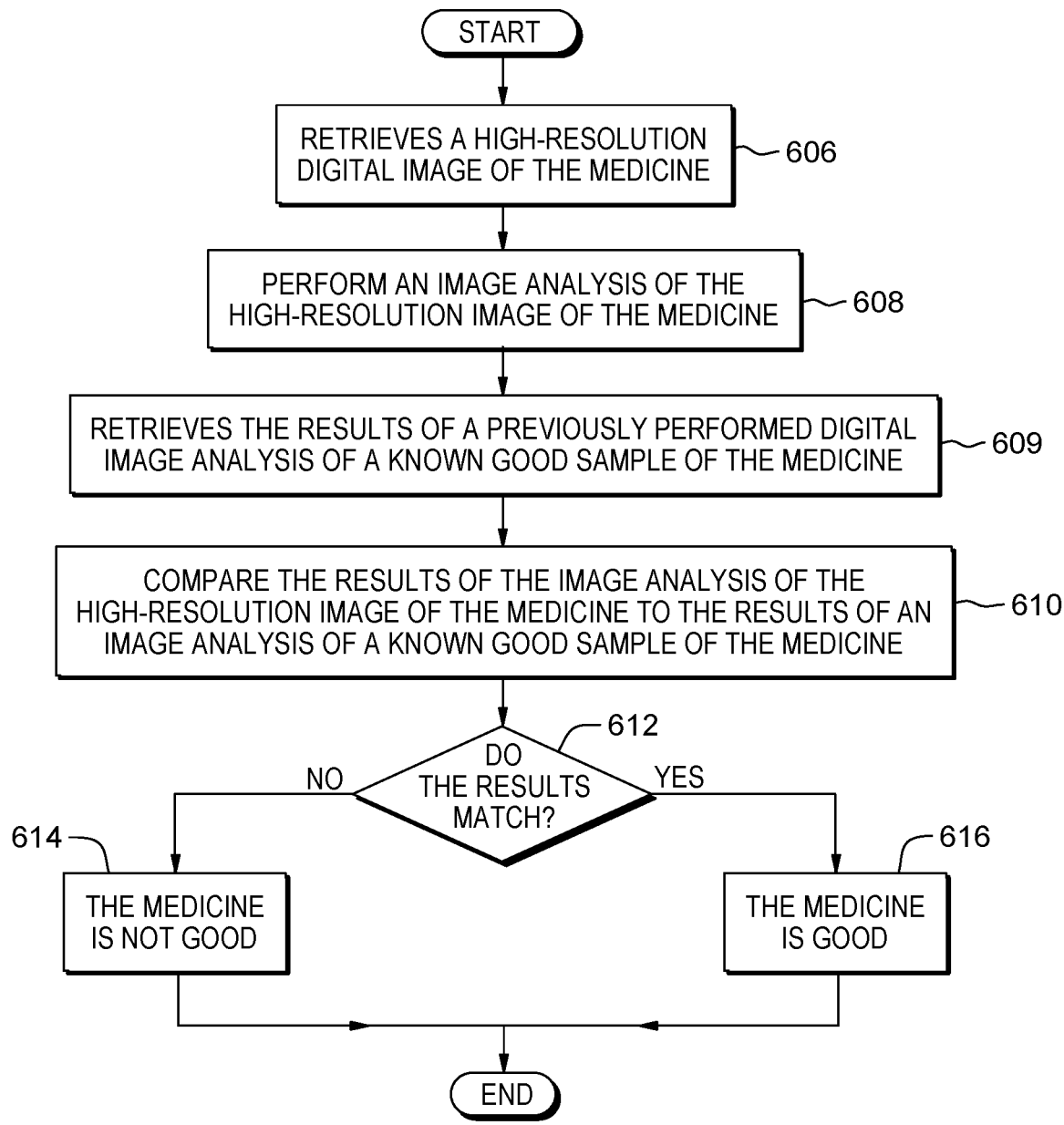
FIG. 6 is a flow chart diagram depicting operational steps for testing the liquid medicine in the vial with the embedded optical lens in the bottom of the vial using an image analysis application in the smart phone, in accordance with at least one embodiment of the invention.

FIG. 6 is a flow chart diagram depicting operational steps for image analysis application 18, in accordance with at least one embodiment of the invention. In various embodiments, image analysis application 18 determines if medicine 11 in a container, such as, vial 30 is authentic or is a counterfeit medicine. While the operation steps of image analysis application 18 in FIG. 6 are discussed with respect image analysis application 18 in smart phone 17, in other embodiments, the operational steps of FIG. 6 also apply to a program with the same functionality and operational steps that resides in another computing device. Additionally, the operational steps of image analysis application 18 in FIG. 6 are discussed with regard to medicine 11 in vial 30, in other embodiments, the operational steps of image analysis application 18 are applicable to medicine 11 in vial 10.

In step 606, image analysis application 18 retrieves a high-resolution digital image of medicine 11 in response to a user input. Imaging analysis application 18 retrieves a high-resolution image of medicine 11 in vial 30. In various embodiments, the high-resolution digital image data of medicine 11 is retrieved from one of persistent storage 705 in smart phone 17 (depicted in FIG. 7), a database, a storage location in a digital camera, or in another computing device.

In step 608, image analysis application 18 performs an image analysis of the captured high-resolution digital image of medicine 11 in vial 30. In various embodiments, image analysis application 18 performs the digital image analysis using known image analysis techniques. For example, as previously discussed, one or more of a known method of hue, saturation, value (HSV) color space analysis or an RGB color space analysis can be used by image analysis application 18 in the digital image analysis. In some examples, when the digital image analysis is an HSV color image analysis of the high-resolution digital image of medicine 11, numerical values can be determined for the saturation, the hue, and the value of each pixel of the high-resolution digital image of medicine 11. The distribution of HSV values in the digital image of medicine 11 may also be determined. In other examples, an RGB color analysis of the digital image data of medicine 11 or another known method of digital image analysis can be used or a combination of digital image analysis methods can be used to precisely analyze the captured high-resolution digital image of medicine 11. In an embodiment, the digital image analysis of retrieved digital images of medicine 11 is performed by a computer program in another computing device.

In step 609, image analysis application 18 retrieves the results of a previously performed digital image analysis of a known good sample of medicine 11 based on a user input. In various embodiments, image analysis application 18 retrieves the results of a digital image analysis of a known good sample of medicine 11 that was taken under the same conditions (e.g., in another vial 30 with optical lens 34, with the same positioning, with the same lighting, etc.) and analyzed under the same application parameters or settings in image analysis application 18. The digital image of the known good sample of medicine 11 is also a high-resolution digital image that is analyzed, for example, using the same digital image analysis techniques as the analysis of medicine 11 in vial 30 in step 608 (e.g., using HSV color analysis). The results of the previous analysis of the known good samples of medicine 11 can be retrieved from storage in smart phone 17 or a storage location in another computing device.

In step 610, image analysis application 18 compares the results of the digital image analysis of the high-resolution digital image of medicine 11 in vial 30 to be evaluated to the results of the digital image analysis of known good samples of medicine 11. In various embodiments, image analysis application 18 in smart phone 17 performs a comparison of the results of the digital image analysis of medicine 11 in vial 30 to the results of the digital image analysis of the known good samples of medicine 11 in a different vial 30. In one embodiment, the comparison of the results of the digital image analysis of medicine 11 in vial 30 and the digital image analysis of the known good sample of medicine 11 is performed by one of a medical professional or a computer program in another computing device.

In decision step 612, image analysis application 18 determines whether the result of the digital image analysis of medicine 11 in vial 30 matches the result of the digital image analysis of the known good samples of medicine 11. In various embodiments, image analysis application 18 in smart phone 17 determines whether the result of the image analysis of the high-resolution digital images of medicine 11 matches the result of the image analysis of the high-resolution digital images of the known good samples of medicine 11. For example, if the numerical value determined by image analysis application 18 for each of the saturation, hue, and value for the high-resolution digital images of medicine 11 in vial 30 are the same numerical value or is within a pre-determined range as the numerical value determined for the saturation, hue, and value of the high-resolution digital images of the known good sample of medicine 11 then, the result of the image analysis of the high-resolution digital image of medicine 11 in vial 30 matches the result of the analysis of the image analysis of the known good samples of medicine 11. Determining whether the results of the two image analyses (e.g., the known good sample and the sample of medicine 11 to be evaluated) match can be done by one of image analysis application 18 in smart phone 17, a computer program in another computing device with the algorithms or computer code of image analysis application 18, or by a medical professional.

Responsive to image analysis application 18 determining that the result of the image analysis of medicine 11 in vial 30 matches the result of the image analysis of the known good samples of medicine 11 ("yes" branch of decision step 612), in step 614, image analysis application 18 determines that medicine 11 in vial 10 is authentic or good (e.g., medicine 11 has the correct active ingredients and amounts of each of the active ingredients). When the results of the image analysis of medicine 11 in the vial matches the results of the image analysis of the known good samples of medicine 11 then, medicine 11 is authentic or good. In this case, the evaluated medicine 11 in vial 30 can be safely taken by a patient. When the comparison is complete, the method of analyzing medicine 11 in vial 30 is over (e.g., the analysis of medicine 11 by image analysis application 18 ends).

Responsive to image analysis application 18 determining that the result of the digital image analysis of medicine 11 in vial 30 does not match the result of the digital image analysis of the known good samples of medicine 11 ("no" branch of decision step 612), in step 616, image analysis application 18 determines that medicine 11 in vial 30 is counterfeit (e.g., medicine 11 in vial 30 does not have the correct active ingredients and/or the correct dosage of each active ingredient). For example, in some cases, the results of the digital image analysis do not match because medicine 11 in vial 30 is diluted and does not have the correct dosage or amount of one or more active ingredients. Therefore, medicine 11 in vial 30 cannot be safely taken by a patient and is discarded or returned to the manufacturer. In some embodiments, image analysis application 18 provides an output, such as a report, detailing the results of the image analysis of both medicine 11 in vial 30 and the results of the image analysis of the known good sample of medicine 11. The method of analyzing medicine 11 in vial 30 using image analysis application 18 is complete (e.g., the analysis of medicine 11 by image analysis application 18 ends).

The flowchart and illustrations in the Figures illustrate a structure, a functionality, and operation of possible implementations of the hardware, such as medicine caps, optical lens, vials, test boxes, computer systems, and computer program or applications according to various embodiments of the present invention. In some alternative implementations, the functions noted in the flow chart may occur out of the order noted in the Figures. For example, two blocks shown in succession may, in fact, be executed substantially concurrently, or the blocks may sometimes be executed in the reverse order, depending upon the functionality involved.

Figure 7:
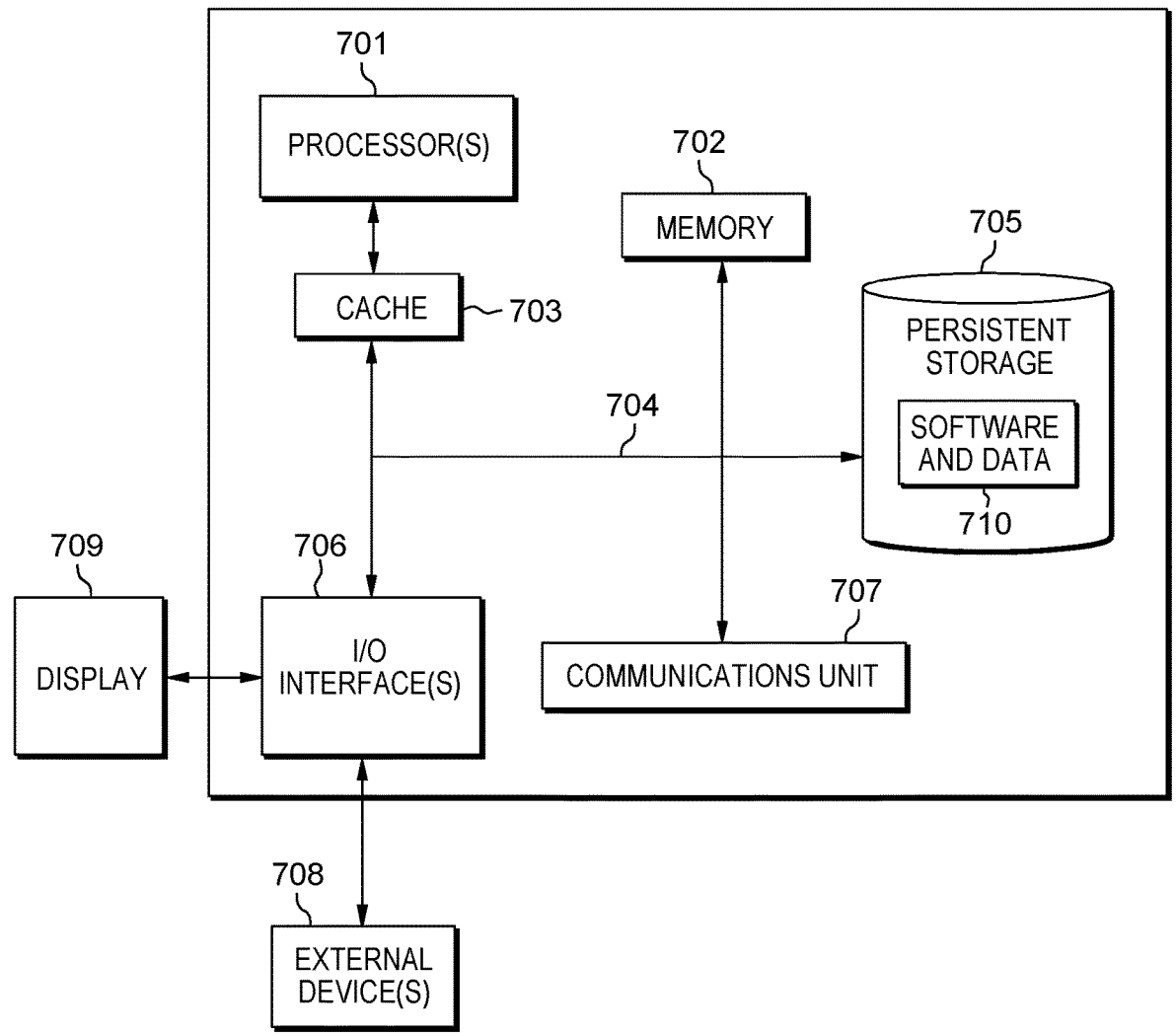
FIG. 7 is a block diagram depicting components of a computer system suitable for executing the image analysis application in the smart phone according to an embodiment of the present invention.

FIG. 7 is a block diagram depicting components of a computer system suitable for executing image analysis application 18 in smart phone 17, in accordance with at least one embodiment of the invention. FIG. 7 depicts a computer system, which is representative of smart phone 17, in accordance with an illustrative embodiment of the present invention. It should be appreciated that FIG. 7 provides only an illustration of one implementation and does not imply any limitations with regard to the environments in which different embodiments may be implemented. The components of computer system of FIG. 7 are suitable for executing image analysis application 18 or a computer program in another computer device to determine if a liquid, such as medicine 11, has the correct active ingredients and the correct amount of each active ingredient. Many modifications to the depicted environment may be made. The computer system of FIG. 7 includes processor(s) 701, cache 703, memory 702, bus 704, persistent storage 705, communications unit 707, input/output (I/O) interface(s) 706, and communications unit 707. Communications unit 707 provides communications between cache 703, memory 702, persistent storage 705, communications unit 707, and input/output (I/O) interface(s) 706. Communications unit 707 can be implemented with any architecture designed for passing data and/or control information between processors (such as microprocessors, communications and network processors, etc.), system memory, peripheral devices, and any other hardware components within a system. For example, communications unit 707 can be implemented with one or more buses or a crossbar switch.

Memory 702 and persistent storage 705 are computer readable storage media. In this embodiment, memory 702 includes random access memory (RAM). In general, memory 702 can include any suitable volatile or non-volatile computer readable storage media. Cache 703 is a fast memory that enhances the performance of processor(s) 701 by holding recently accessed data, and data near recently accessed data, from memory 702. In various embodiments, memory 702 and persistent storage 705 may store data including digital image data of medicine 11 and the results of the digital image analysis of both known good samples of medicine 11 and samples of medicine 11 being evaluated by image analysis application 18.

Program instructions and data (e.g., software and data 710) used to practice embodiments of the present invention may be stored in persistent storage 705 and in memory 702 for execution by one or more of the respective processor(s) 701 via cache 703. In an embodiment, persistent storage 705 includes a magnetic hard disk drive. Alternatively, or in addition to a magnetic hard disk drive, persistent storage 705 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 705 may also be removable. For example, a removable hard drive may be used for persistent storage 705. Other examples include optical and magnetic disks, thumb drives, and smart cards that are inserted into a drive for transfer onto another computer readable storage medium that is also part of persistent storage 705. Software and data 710 can be stored in persistent storage 705 for access and/or execution by one or more of the respective processor(s) 701 via cache 703. With respect to smart phone 17, software and data 910 includes image analysis application 18.

Communications unit 707, in these examples, provides for communications with other data processing systems or devices. In these examples, communications unit 707 includes one or more network interface cards. Communications unit 707 may provide communications through the use of either or both physical and wireless communications links. Program instructions and data (e.g., software and data 710) used to practice embodiments of the present invention may be downloaded to persistent storage 705 through communications unit 707.

I/O interface(s) 706 allows for input and output of data with other devices that may be connected to each computer system. For example, I/O interface(s) 706 may provide a connection to external device(s) 708, such as a keyboard, a keypad, a touch screen, and/or some other suitable input device. External device(s) 708 can also include portable computer readable storage media, such as, for example, thumb drives, portable optical or magnetic disks, and memory cards. Program instructions and data (e.g., software and data 710) used to practice embodiments of the present invention can be stored on such portable computer readable storage media and can be loaded onto persistent storage 705 via I/O interface(s) 706. I/O interface(s) 706 also connect to display 709.

Display 709 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute a resource entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. An apparatus, for sealing a container, comprising a cap with an embedded lens comprising:
    a flat round top portion of a cap with a circular opening in the cap;
    a sampling insert inside the circular opening in the flat round top portion of the cap; and
    a lens embedded inside the circular opening in the cap.

2. The apparatus of claim 1, wherein the embedded lens is a high-resolution optical lens.

3. The apparatus of claim 1, wherein the lens embedded inside the circular opening in the cap provides a view of a liquid in the container.

4. The apparatus of claim 1, wherein the cap is composed of a material selected from a group consisting of: a plastic material, a rubber material, and a metal material.

5. The apparatus of claim 1, wherein a gasket is in the circular opening in the cap between the cap and the lens.

6. The apparatus of claim 1, wherein the lens has a sub-micron resolution.

7. A sampling insert and a high-resolution lens embedded in a cap that seals a container holding a liquid, the cap comprising:
   a top flat portion of a cap with an opening in a top flat portion of the cap;
   a sampling insert inside the opening in the top flat portion of the cap; and
   a high-resolution lens inside an opening in the sampling insert.

8. The cap of claim 7, wherein the high-resolution lens has a sub-micron resolution.

9. The cap of claim 7, wherein the sampling insert inside the opening in the top flat portion of the cap has a rectangular outer edge shape when the opening in the cap is rectangular and a circular inside edge shape to hold the high-resolution lens inside the opening in the sampling insert.

10. The cap of claim 7, wherein the sampling insert is composed of a soft material allowing insertion of a syringe through the sampling insert inside the opening in the top flat portion of the cap.

11. A liquid container with a high-resolution lens in a bottom portion of the liquid container, the liquid container comprising:
   a bottom portion of a liquid container with an opening;
   a sampling insert inside the opening in the bottom portion of the liquid container;
   and a high-resolution lens in the opening in the bottom portion of the liquid container.

12. The liquid container of claim 11, wherein the opening in the bottom portion of the container is a circular opening holding the high-resolution lens in the bottom portion of the liquid container.

13. The liquid container of claim 11, wherein the high-resolution lens has a sub-micron resolution.

14. The liquid container of claim 11, wherein the liquid container is composed of a transparent material.

15. The liquid container of claim 11, wherein a gasket is between the opening in the bottom portion of the liquid container and the high-resolution lens, and wherein the high-resolution lens has a sub-micron resolution.

16. A method of testing a first liquid in a first container with a high-resolution lens in a bottom portion of the first container, the method comprising:
   placing a first container with a high-resolution lens in a bottom portion of the first container in a test box with the high-resolution lens in the bottom portion of the first container positioned over an opening in a bottom portion of the test box;
   positioning a digital image capture device under the test box, wherein the digital imaging device is positioned under the opening in the bottom portion of the test box and under the high-resolution lens in the bottom portion of the first container; and
   capturing a first high-resolution digital image of the first liquid in the first container through the high-resolution lens in the bottom portion of the first container.

17. The method of testing the liquid in the container of claim 16, further comprising:
   retrieving, by a computer program in a computing device, the first high-resolution digital image of the first liquid in the first container taken through the high-resolution optical lens in the bottom portion of the container;
   retrieving, by the computer program in the computing device, from storage, a result of a second image analysis of a second high-resolution digital image of a known good sample of a second liquid in a second container;
   performing, by the computer program in the computing device, an image analysis of the first high-resolution digital image of the first liquid in the first container;
   comparing, by the computer program in the computing device, a result of the image analysis of the first high-resolution digital image of the first liquid in the first container with the result of the image analysis of the second high-resolution digital image of the sample of a known good sample of the second liquid in the second container;
   determining, by the computer program in the computing device, whether the result of the image analysis of the first high-resolution digital image of the first liquid in the first container matches the result of the image analysis of the second high-resolution digital image of the sample of a known good sample of the second liquid in the second container; and
   responsive to determining that the results of the image analysis of the first high-resolution digital image of the first liquid in the first container do not match the result of the image analysis of the sample of the known good sample of the second liquid in the second container, determining, by the computer program in the computing device, that the first liquid in the first container is counterfeit.

18. The method of claim 16, wherein the test box is a transparent rectangular test box, and wherein the opening in the bottom portion of the test box is larger than the high-resolution lens in the bottom portion of the first container and smaller than the bottom portion of the first container.

19. A computer program product, for testing a liquid in a container, the computer program product comprising:
   one or more non-transitory computer readable storage media; and
   program instructions stored on the one or more computer readable storage media, the program instructions executable by one or more computer processors, the program instructions comprising instructions for:
   retrieving, by the one or more computer processors, based on an input by a user, a high-resolution digital image of a first liquid in a first container;
   performing, by the one or more computer processors, a first image analysis of the first high-resolution digital image of the first liquid in the container;
   retrieving, by the one or more computer processors, a result of a second image analysis of a second high-resolution digital image of a known good sample of a second liquid in a second container from storage, based on the input by the user;
   comparing, by the one or more computer processors, a result of the first image analysis of the first high-resolution digital image of the first liquid in the first container to the result of the second image analysis of the second high-resolution digital image of the known good sample of the second liquid in the second container; and
   determining, by the one or more computer processors, whether the result of the first image analysis of the first high-resolution digital image of the first liquid in the first container and the result of the second image analysis of the second high-resolution digital image of the known good sample of the second liquid in the second container match, wherein the second liquid in the second container is a known good sample of the first liquid in the first container, and wherein determining whether the result of the first image analysis of the first high-resolution digital image of the first liquid in the first container and the result of the second image analysis of the second high-resolution digital image of the known good sample of the second liquid match includes determining, by the one or more computer processors, that each active ingredient in the second liquid in the second container is present in the first liquid in the first container.

20. The computer program product of claim 19, wherein the first image analysis of the first high-resolution digital image data of the first liquid in the first container is a first hue, saturation, and value color analysis of first digital image of the first liquid in the first container and the second image analysis of the second high-resolution digital image of the known good sample of the second liquid in the second container is a second hue, saturation, and value analysis of the second high-resolution digital image of the known good sample of the second liquid in the second container.

21. The computer program product of claim 20, wherein determining whether the result of the first image analysis of the first high-resolution digital image of the first liquid in the first container and the result of the second image analysis of the second high-resolution digital image of the known good sample of the second liquid match in the second container includes determining, by the one or more computer processors, that the first hue, saturation, and value analysis of the first digital image of the first liquid in the first container matches the second hue, saturation, and value analysis of the second high-resolution digital image of the known good sample of the second liquid in the second container.

22. The computer program product of claim 19, wherein responsive to determining that the result of the first image analysis of the first high-resolution digital image of the first liquid in the first container and the result of the second image analysis of the second high-resolution digital image of the known good sample of the second liquid do not match, determining, by the one or more computer processors, that the first liquid in the first container is counterfeit.

23. The computer program product of claim 19, wherein the first high-resolution digital image of the first liquid in the first container is one of the high-resolution digital image of the first liquid in the first container that is one of captured through a high-resolution optical lens embedded in a cap sealing the first container or the high-resolution digital image of the first liquid in the first container that is captured through a high-resolution optical lens embedded in a bottom portion of the first container.

\* \* \* \* \*